US005762936A

United States Patent [19]
Ronzio et al.

[11] Patent Number: 5,762,936
[45] Date of Patent: Jun. 9, 1998

[54] ANTIOXIDANT DERIVED FROM LENTIL AND ITS PREPARATION AND USES

[75] Inventors: Robert A. Ronzio; David N. Muanza. both of Houston; William S. Sparks. Bellaire. all of Tex.

[73] Assignee: Biotics Research Corporation. Stafford. Tex.

[21] Appl. No.: 707,723

[22] Filed: Sep. 4, 1996

[51] Int. Cl.$^6$ .................................................. A01N 65/00
[52] U.S. Cl. ........................................................ 424/195.1
[58] Field of Search .................. 424/195.1; 426/615, 426/629, 634

[56] References Cited

PUBLICATIONS

Sosulski et al. "Composition of free and hydrolyzable phenolic acids in the flours and hulls of ten legume species". J. Agric. Food Chem. (1984) 32: 131–133, 1984.

Nozzolillo et al. "Browning of lentil seeds, concomitant loss of viability, and the possible role of soluble tannins in both phenomena". Can. J. Plant Sci. (1984) 64:815–824, 1984.

Griffiths, "The Polyphenolic Content . . . of . . . Bean" J. Sci. Food Agric. 1981, 32 pp. 797–804.

Tsuda et. al "Antioxidative Activity of . . . Cyanidiu" J. Agric. Food Chem. 1994, 42, 2407–2410.

Tsuda et. al.. "Antioxidative Components . . . from . . . Tamarind" J. Aric. Food Chem, 1994, 42, pp. 2671–2674.

Sabry et al.. "Phenolics . . . of . . . Lens Esculenta . . . " Rev. Latinoamer. Quim 18(2) 88–88 (1987).

Robeson "Furanoacetylene . . . in Lens culinaris" Phytochemistry 17(4) pp. 807–808 (1978) (Database Abs.).

D'Arcy et. al "Les Flavonoides . . . Lens Culinaris"Phytochemistry 17(4) 826–827 (1978) (in French).

Vaillancourt et al ". . . Tannin Concentration in Lentil" Can J Plant Sci 66:241–246 (1986).

Tsuda et al.. "Antioxidative Pigments . . . from . . . Phaseolus . . . " J Agric Food Chem 1994, 42, 248–251.

*Primary Examiner*—Jean C. Witz
*Assistant Examiner*—Susan Hanley
*Attorney, Agent, or Firm*—John R. Casperson

[57] ABSTRACT

The preparation of extracts of seed coats of lentil (*Lens esculenta*) as a representative member of the Leguminosae. extracted with a range of volatile solvents, such as methanol. acetone, singly or a mixture with water, and food solvents, such as ethyl acetate and ethanol, to yield such extracts that are water-soluble, which contain a rich mixture of condensed tannins (procyanidins and prodciphinidin as glycosides), together with a flavanone (luteolin) and flavonols (quercetin, kaempferol) and phenolic acids (ferulic acid, protocatechuic acid, caffeic acid) and which possess the ability to quench organic free radicals, to scavenge superoxide, to inhibit the oxidation of water soluble nutrients such as vitamin C, as well as the oxidation of fat-soluble nutrients such as essential fatty acids, and to limit damage due to oxidants linked to inflammatory conditions, and to inhibit certain cells responsible for inflammation, is disclosed.

21 Claims, No Drawings

5,762,936

ANTIOXIDANT DERIVED FROM LENTIL AND ITS PREPARATION AND USES

BACKGROUND OF THE INVENTION

In one aspect, the invention relates to an antioxidant derived from lentil seed husks. In another aspect, the invention relates to a process for preparing the antioxidant. In yet another aspect, the invention relates to uses for the antioxidant.

Plant seed coats sometimes possess antioxidants that protect the seed and embryo against oxidative damage during seed storage and germination. For example, the antioxidative components of seed coats of tamarind (*Tamrindus indica L.*) were studied by Tsuda et al (J. Agric. Food Chem. 1994:42:2641–2674). Seed coats were extracted with ethanol, ethyl acetate, an ethyl acetate-ethanol mixture or methanol. All of the solvent extracts inhibited the oxidation of linoleic acid, with the ethyl acetate extract being somewhat more active. The major active components were identified as ethyl 3,4 dihydroxybenzoate, 2-hydroxy 3,4 dihydroxyacetophenone, 3,4 dihydroxyphenyl acetate and epicatechin. Essentially no antioxidant activity was detected in the germ.

It was reported in Tsuda et al. (J. Agric. Food Chem. 1994:42:248–251) that pigments from red and green pea bean (*Phaseola vulgaris L.*) blocked the autoxidation of linoleic acid. Pelargonidin glucoside, delphinidin glucoside and cyanidin glucoside were identified in an extract prepared from 0.5% trifluroacetic and 80% ethanol. Later studies demonstrated that cyanidin and its glucoside block lipid peroxidation of erythrocyte membranes and liposomes. (Tsuda et al., J. Agric. Food Chem. 1994:42:2407–10).

d'Arcy and Jay (Phytochemistry 17 (4) 826–827 (1978)) reported the polyphenols isolated from *Lens culanaris* seed coats include tricetin, luteolin, a diglycosyldelphinidin and two proanthocyanidins. The germ contained mainly a kaempferol glycoside and 5-deoxykaempferol.

Masquelier, U.S. Pat No. 4,698,360, Oct. 6, 1987 disclosed the isolation of a fraction enriched in proanthocyanidins from pine bark which possesses free radical scavenging effects. The therapeutic use of the extracts is proposed for vascular pathologies, tumor promotion, hypoxia following atherosclerosis and cerebral involution associated with aging.

Normal cellular antioxidant defenses, consisting of enzymes (catalase, superoxide dismutases, glutathione peroxidases), antioxidant nutrients and endogenously formed antioxidants, can be impaired by environmental exposure to toxic materials including medications and pollutants, disease processes, as well as inadequate nutrition. Free radicals and reactive oxygen species can attack DNA, leading to mutations and faulty repair mechanisms, as well as proteins, thus altering enzyme, surface receptor and other essential functions. Attack on lipids in cell membranes and in low density lipoproteins leads to the peroxidation of unsaturated fatty acid constituents with the possibility of initiating chain reactions. Possible altered physiologic function include the incorporation of oxidized LDL into atherosclerotic lesions, a proposed early event in the disease process.

Free radicals and oxidative stress, that is the overproduction of reactive oxygen-containing molecules, has been associated with nearly 100 disorders, including certain types of cancer, retinal degeneration, cardiovascular disease, neurodegenerative diseases, ischemia-reperfusion, autoimmune conditions and other conditions associated with chronic inflammation. Whether or not free radicals or reactive oxygen species are a cause or a consequence of the condition, there are strong indications that antioxidant supplementation can at least ameliorate several of these conditions, including coronary artery disease, cataract, stroke rheumatoid arthritis, inflammatory bowel disease, radiation injury, iron overload disease among other (Kehrer J. P. et al., Free radicals in biology: sources, reactivities and roles in the etiology in human diseases. In Natural Antioxidants In Human Health and Disease, Academic Press 1994, 24–62); Ames et al., Proc. Natl. Acad. Sci. 1993, 90:7915–7922; Halliwell, Am. J. Med. 1991, 91(suppl C) 14S–22S).

The free radical theory of aging (Harman, D., Drugs Aging 1993; 3:60–80) proposes that the body's antioxidant and repair mechanisms are not 100% effective, so that over time, damage to DNA and other cell constituents gradually accumulates. Ultimately a point is reached at which the cell can no longer function effectively, tissue and organ integrity is compromised, setting the stage for degenerative diseases and cancer. Dietary antioxidants influence the course of these events.

Flavonoids possess many properties in addition to their antioxidant functions. For example, flavonoids can inhibit platelet aggregation, to diminish the risk of blood clot formation. By virtue of effects on the body's detoxication systems, flavonoids are known to inhibit the initiation of certain cancers. By inhibiting intracellular signalling mechanisms, they can block cancer promotion as well (Pathak et al., Fitoterapia, 1991, 62:471–389).

Antioxidants to inhibit the oxidation of water soluble nutrients, such as vitamin C, and essential fatty acids, such as linoleic acid, are desirable for improving human nutrition. Antioxidants are also desirable for their use in treating disease and in slowing the aging process. Natural antioxidants which can be derived from an inexpensive food source are especially sought after.

OBJECTS OF THE INVENTION

It is an object of this invention to obtain an extract of lentil seed coats that is highly enriched in polyphenolic and other species that possess a broad range of antioxidant activities against free radicals, including superoxide and other reactive oxygen species.

It is further object of this invention to prepare an antioxidant mixture that is compatible with aqueous media to facilitate uptake of assimilation.

It is a another object of this invention to minimize prooxidants found in whole lentils.

It is another object of this invention to stabilize and protect edible foods, food isolates and beverages derived from them, as well as dietary supplements, animal feeds and therapeutics based on studies of human cells to decrease the risk of chronic conditions associated with free radical and oxidant stress, and to limit the excessive activity of proinflammatory cells.

SUMMARY OF THE INVENTION

In one embodiment of the invention, there is provided a process for producing a water-soluble antioxidant from lentil. The process is carried out by first providing a quantity of lentil seed coats. A soluble fraction of the lentil seed coats is extracted using water and at least one volatile organic solvent to produce a mixture of liquids containing lentil seed coat extract and solids. The liquids are separated from the solids. The water and at least one volatile organic solvent are then separated from the lentil seed coat extract to produce the water-soluble antioxidant.

Alternatively, a soluble fraction of the lentil seed coats can be extracted using hot water to produce an aqueous phase containing lentil seed coat extract and solids. A portion of the lentil seed coat extract is separated as a precipitate from the aqueous phase. The aqueous phase is separated from the solids and the precipitate to produce a clarified aqueous phase. The clarified aqueous phase is extracted with a volatile organic solvent to produce a solvent extract of lentil seed coat. The volatile organic solvent is separated from the solvent extract to produce the water soluble antioxidant.

Lentil is an accepted foodstuff and the antioxidants contained therein are concentrated in the seed coat. The seed coat extract also does not contain some pro-oxidant species found in the germ. The recovered material contains over 70% of the tannin material-like material (measured as catechin equivalents) and it possesses a range of antioxidant species. A variety of accepted food grade solvents can be used for the extraction, and the extraction is simple and direct and produces a new and improved antioxidant herbal extract which is water soluble and enriched in the major phenolic compounds of lentil.

The resulting extract is characterized by a phenolics content in the range of from about 1 to about 6 milligrams of catechin equivalents per 10 milligrams of extract. In the form in which it is recovered from the above processes, it contains kaempferol, quercetin, proanthocyanidins including procyanidin and prodelphinidin as glycosides, and phenolic acids including ferulic acid, protocatechuic acid and caffeic acid. The extract is highly effective at reducing organic free radicals and superoxide, and thus is a potent antioxidant.

In accordance with another embodiment of the invention, the extract, or a component thereof, is used to inhibit the oxidation of materials intended for human or animal ingestion. The method is carried out simply by incorporating into the materials an amount of the extract, sufficient to inhibit oxidation of the materials. This aspect of the invention is believed to have good utility for inhibiting the oxidation of vitamin C and linoleic acid for use as human nutritional supplements.

In accordance with another embodiment of the invention, the extract, or a component thereof, is used in the treatment of a patient having a condition of tissue inflammation. The method is carried out simply by administering to the patient an amount of the extract which is sufficient to reduce the inflammation. This aspect of the invention is believed to have good utility for treating conditions of chronic inflammation, such as colitis, lupus erythematoscis, rheumatoid arthritis, ischemia, and alcoholic liver disease. It is believe the invention will also be used in treating tissue inflammation resulting from an injury, such as thermal and sun trauma, toxin exposure, excessive physical activity, radiation exposure, and infections. It is believed that the extract will be highly effective in the treatment of chronic intestinal inflammation when administered orally. Because this condition is difficult to effectively treat by known methods, the invention is a significant advance.

In another embodiment of the invention, there is provided a method for inhibiting oxidation-induced apoptosis in healthy human cells. The method is carried out by maintaining the cells in the presence of a sufficient concentration of the extract to inhibit oxidation-induced apoptosis. In a preferred embodiment, the method would be carried out by using the extract as a human dietary supplement to ameliorate the effects of aging or oxidation-induced cell damage caused by diet, exposure to medications or toxins, or disease process.

In yet another embodiment of the invention, there is provided a method for causing necrotic cell death in cancerous human cells. The method is carried out by exposing the cells to a sufficient concentration of the extract to cause the necrotic cell death of a portion of such cells. The extract has low toxicity to normal cells and high toxicity to certain cancer cells.

In a further embodiment of the invention, there is provided a method for selectively inhibiting the viability of human macrophage cells without inhibiting the viability of other healthy human cells found in close association with the macrophage cells. The method is carried out maintaining both the macrophage cells and the other healthy cells in the presence of a concentration of least one component found in the extract which is sufficiently high to inhibit the viability of the macrophage cells but too low to inhibit the viability of the other healthy cells which are in close association with the macrophage cells. Excess macrophage numbers are involved in the pathologies of certain chronic inflammation syndromes and their selective destruction or inhibition would be beneficial to patients afflicted with such syndromes.

DETAILED DESCRIPTION OF THE INVENTION

Process for producing a water-soluble antioxidant from lentil

The process is carried out by first providing a quantity of lentil seed coats. A soluble fraction of the lentil seed coats is extracted using water and at least one volatile organic solvent to produce a mixture of liquids containing lentil seed coat extract and solids. The liquids are separated from the solids. The water and the at least one volatile organic solvent are then separated from the lentil seed coat extract to produce the water-soluble antioxidant.

Food grade lentils range in color from green to brown. The literature indicates that the color change reflects storage conditions of the lentil seed, among other factors. Both types are applicable to the invention. Although any variety of lentil can be used in the invention, seed coat from the seeds of domestic varieties of *Lens esculenta* is preferred, since it has been tested with good results.

The coats or husks can be separated from the germ or cotyledon by any means, such as manually or by sieving. Soaking the whole lentils for several hours in water facilitates the separation. The coats are then preferably dried and milled to a powder, more preferably a fine powder.

Generally speaking, the at least one volatile organic solvent consists of carbon, oxygen and hydrogen, because such solvents have relatively low human toxicity. Usually, the at least one volatile organic solvent contains four or fewer carbon atoms, for reasons of volatility and extraction efficacy, and is selected from the group consisting of an alcohol and a ketone, for reasons of efficacy and low toxicity. Preferably, the at least one volatile organic solvent is selected from the group consisting of methanol, ethanol and acetone, which have been tested with good results.

The liquids can be separated from the solids by any convenient means, such as by filtration. The water and the at least one volatile organic solvent are preferably separated from the lentil seed coat extract at a temperature which does not exceed 40° C., in order to preserve the antioxidant properties of the extract. Vacuum distillation can be employed with good results. The final powder is preferably then dried at low temperature, such as by vacuum drying.

Alternatively, a soluble fraction of the lentil seed coats can be provided using hot water extraction to produce an aqueous phase containing lentil seed coat extract and solids. A portion of the lentil seed coat extract is separated as a precipitate from the aqueous phase. The aqueous phase is separated from the solids and the precipitate to produce a clarified aqueous phase. The clarified aqueous phase is extracted with a volatile organic solvent to produce a solvent extract of lentil seed coat. The volatile organic solvent is separated from the solvent extract to produce the water soluble antioxidant.

The hot water extraction can be carried out at a temperature between about 25° C. and 100° C. but is preferably carried out at near 100° C. Precipitation is made to occur by adding salt to the aqueous phase. Sodium chloride provides good results. Separation of solids from the aqueous phase, such as by filtration, is conducted before and/or after, preferably after, the precipitation step. The volatile organic solvent can be of the types mentioned previous, but ethyl acetate is preferred because it has been used with good results.

The antioxidant composition

The extraction steps yield a concentrated pigmented residue which dissolves completely in water, reduces organic free radicals, quenches superoxide, inhibits the peroxidation of linoleic acid, and inhibits the oxidation of reduced ascorbic acid. The extract is characterized by a phenolics content in the range of from about 1 to about 6 milligrams of catechin equivalents per 10 milligrams of extract, preferably in the range of from about 2 to about 4 milligrams of catechin equivalents per 10 milligrams of extract.

The phenolics are predominantly in the form of polyphenols, including flavonoids and phenolic acids.

The flavonoids include flavones, flavanols and condensed tannins. The flavones include luteolin. The flavanols include quercetin and kaempferol. The condensed tannins are in the form of proanthocyanidins including procyanidin, prodelphinidin and their glycosides.

The phenolic acids include ferulic acid, protocatechuic acid, and caffeic acid.

The preferred composition contains kaempferol, quercetin, proanthocyanidins including procyanidin and prodelphinidin as glycosides, and phenolic acids including ferulic acid, protocatechuic acid and caffeic acid. Generally speaking, at least 50% by weight, preferably at least 70% by weight, of the proanthocyanidin is in the form of prodelphinidin.

Using the extraction procedures employed herein, prodelphinidin accounts for at least about 15% by weight, preferably greater than about 20% by weight, of the extract. This amount corresponds to about 0.66% to about 1.04% of the lentil hull. This is on the order of 4 times greater than values previously reported by d'Arcy and Jay (1975). Phrased another way, the extraction procedures employed herein recover a much greater amount of the prodelphinidin than the prior art techniques and produce an extract having a much higher level of prodelphinidin than prior art techniques.

The extract is preferably further characterized by the substantial absence of prooxidant species. Such species can be found in the germ of the lentil, but are removed by the separation process described above.

The ability of the extract to reduce organic free radicals is described in terms of its ability to reduce dipicrylhydrazyl radical. Generally speaking, the extract has an IC50 in the range of from about 1.5 to about 15 micrograms per milliliter as measured by reduction of dipicrylhydrazyl radical, preferably in the range of from about 4.04 to about 14.83 micrograms per milliliter.

The ability of the extract to reduce superoxide is determined by following the reduction of nitro blue tetrazolium by superoxide. Generally speaking, the extract has an IC50 in the range of from about 1 to about 10 micrograms per milliliter as measured by reduction of nitro blue tetrazolium by superoxide, preferably in the range of from about 3 to about 6 micrograms per milliliter, and most preferably in the range of from about 4 to about 5 micrograms per milliliter.

Use as a preservative

Lentil husk extract can prevent the oxidation of foodstuffs and nutrients appropriate for human consumption and thus may be added to foods as a food-based preservative. The extract stabilizes a wide range of commonly ingested nutrients.

In accordance with another embodiment of the invention, the extract, or a component thereof, is used to inhibit the oxidation of materials intended for human or animal ingestion. The method is carried out simply by incorporating into the materials an amount of the extract which is sufficient to inhibit oxidation of the materials. The invention can be used with foodstuffs, beverages, livestock feed, nutritional supplements and pharmaceutical agents, for example, but is expected to be especially useful for preventing the oxidation of foodstuffs and beverages intended for human consumption as well as nutritional supplements such as vitamins and essential fatty acids. Test results show that the extract is highly effective in stabilizing linoleic acid and in maintaining ascorbic acid (vitamin C) in a reduced state.

Use to relieve chronic inflammation

The extract, as a potent mixture of water-soluble, plant-based antioxidants, can be used as an antioxidant supplement for humans with the overall goal of preventing or ameliorating chronic degenerative diseases in which chronic inflammation and free radical pathology has been suggested.

This aspect of the invention is carried out by administering to the patient an amount of the extract which is sufficient to reduce the inflammation. It is believed that the invention can be used to treat coronary artery disease, stroke, ischemia-reperfusion, rheumatoid arthritis, autoimmune disorders such as lupus erythematoscis, inflammatory bowel disease such as colitis, radiation injury, iron overload disease, alcoholic liver disease, and other conditions of inflammation such as those due to thermal insult, sun insult, excessive physical activity, toxin exposures, and infections, by administering it orally, intravenously, intramuscularly, or by any other means. It is believed that the extract will be highly effective in the treatment of chronic intestinal inflammation when administered orally. For example, the extract can be administered orally as tablets, capsules, powders or beverages in divided does or as a single bolus to humans as well as to animals as in a veterinary practice. Generally speaking, in the range of from about 2 to about 2,000 milligrams of the extract should be administered to a human patient daily, usually in the range of from about 15 to about 1500 milligrams daily. The amount administered should be sufficient to result in decreased serum or plasma lipid peroxide level or urinary secretion products of lipid peroxidation such as F2 isoprostanoids, and decreased urinary excretion of 8-oxo-guanine and other markers of DNA excision repair of oxidative damage.

On a cellular basis, this aspect of the invention is described as inhibiting oxidation-induced apoptosis in healthy human cells by maintaining the cells in the presence of a sufficient concentration of the extract to inhibit oxidation-induced apoptosis. The concentration of extract which is effective to accomplish this result is generally in the range of from about 1 to about 100 micrograms per milliliter.

Use as an anticancer drug

Tests demonstrate that the extract is toxic to cancer cells. In yet another embodiment of the invention, there is provided a method for causing necrotic cell death in cancerous human cells. The method is carried out by exposing the cells to a sufficient concentration of the extract to cause the necrotic cell death of a portion of such cells. It appears that a concentration in the range of from about 200 to about 2,000 micrograms per milliliter is adequate.

Use for macrophage inhibition

Macrophages are an important part of the body's immune system. They engulf their target cells and destroy them with oxidizing chemicals. Under certain circumstances, the macrophages target healthy cells, causing a variety of autoimmune disorders or syndromes. Rheumatoid arthritis is an example of such a disorder. In other situations, persistent inflammation, induced in part by macrophages, causes tissue damage. Inflammatory bowel disease is an example of such a disorder. An effective treatment for patients suffering from such disorders would be desirable. The extract of the invention selectively inhibits and even destroys excess macrophages. The method is carried out maintaining both the macrophage cells and the other healthy cells in the presence of at a concentration of least one component found in the extract which is sufficiently high to inhibit the viability of the macrophage cells but too low to inhibit the viability of the other healthy cells which are in close association with the macrophage cells. For this application, a concentration of the extract which is in the range of from about 1 to about 100 micrograms per milliliter is believed suitable.

The invention is further illustrated by the following examples.

EXAMPLE I

PREPARATION OF THE EXTRACT a. Preparation of seed coats from brown lentils

Food grade brown lentils (518 g) were immersed in deionized water for 10 hr at room temperature then the lentil seed coats were collected manually. The seed coats were air dried and then milled to a fine powder (designated brown LH). The weight of brown LH was 36.45 g, representing a 7% yield.

b. Preparation of seed coats from green lentils

Lentil seed coats were obtained from 1 Kg of food grade, green lentils. The seeds were first moistened for 12 hr., then sieved to separate the seed coats from the cotyledons. The husks were dried at 40 C. and then milled to a fine powder (designated green LH). The yield was 36.3 g, representing a 3.6% yield.

c. Solvent extraction of seed coats i. Brown LH 3.4 g of brown LH were extracted 4 times with 1 liter of methanol-water (1:1 v/v). In each extraction, the solvent/husk mixture was heated to boiling for 15 minutes and then allowed to stand at room temperature for 10 hr with constant stirring. The suspension was filtered and the dark brown filtrate collected. The combined filtrates were concentrated to dryness by rotary evaporation at 40 C. The yield of brown residue (lentil husk methanol-water extract—LHME) was 758 mg, representing a 22.3% yield based on the initial weight of brown lentil seed coats.

ii. Green LH 150 g of green LH were first washed with methanol (1 L, 4 times) without heating to remove chlorophyll. LH was then extracted 4 times with methanol-water (1:1, v/v) with heating and stirring as described above. The suspension was filtered and the dark brown filtrate was collected. Upon standing a room temperature, a precipitate formed. This was removed by filtration. The combined filtrates were concentrated to dryness by rotary evaporation to yield 13.1 g of dark brown residue (LHME), representing a yield of 8.7 % based on the initial weight of green LH.

EXAMPLE II

CHARACTERIZATION OF THE EXTRACT a. Total phenolic content

The percentage of total phenolic material in LHME from brown seeds and green seeds was determined using the method of Satue et al., J. Am. Oil Chemists Soc. 1995; 72:1131. Solutions were prepared by dissolving dried samples of LHME in water (5 mg/50 ml). The catechin standard (10 mg/100 ml) was dissolved in methanol. After a reaction time of 3 minutes in 2.25% Folin-Ciocalteau reagent, sodium carbonate was added to a concentration of 2%. Absorbance at 750 nm was recorded after 30 min. Results showed that LHME contains 2.33 to 3.03 mg of catechin equivalents per 10 mg of LHME. Thus, 70–80% of the phenolic material of the LH is recovered in the LHME. Recovered phenolic substances account for 3.8 to 5.2% of the dry weight of the LH. This is a significantly greater recovery than the 2.8 to 4.2% of dry weight of seed husks reported by previous investigators.

b. Spectral identification of proanthocyanidins

The UV-visible spectrum of lentil husk seed coat extract in water revealed a maximum absorption at 276 nm, similar to pine bark proanthocyanidins (lambda max 283 nm), and grape seed oligomeric proanthocyanidins (lamba max 279 nm). No absorption was detected between 300 and 900 nm for any of these extracts in their native form.

Hydrolysis of the extracts was performed by heating in 5% hydrochloric acid in butanol for 2 hr at 95 C. This procedure yielded a magenta pigment in all cases. This pigment is ascribed to the filavylium cation ion in acidic solution. This spectral evidence for Bate-Smith reaction has been reported as characteristic for proanthocyanidins and is confirmatory evidence for the identification of this species. Furthermore, the maximum absorbance in the visible region of the spectrum appeared at 555–558 nm, and the spectrum of anthocyanidin from hydrolysis matched delphinidin.

c. Thin layer chromatography of LHME-Detection of phenols and flavonoids

LHME was dissolved in a minimum amount of water methanol and subjected to thin layer chromatography on silica gel plates (0.2 mm gel, GF254). The TLC plates were developed with butanol-acetic acid-water (4:1:2, v/v) at room temperature. The TLC plates were then air dried and exposed to iodine vapor to locate species with unsaturated bonds, or sprayed with Folin-Ciocalteau reagent to visualize phenolic species, or sprayed with ferric chloride reagent containing aluminum chloride in ethanol, in order to visualize flavonoid compounds. The resulting colored complexes fluoresced in UV light at 365 nm. Chromatographic analysis revealed the presence of 10 phenolic spots in LHME, 5 of which tested positive for the pyrogallol moiety (1,2,3 hydroxy derivatives similar to the gallic acid structure). Three species of LHME tested positive for flavonoids. Comigration with reference glycosides, naringin and hesperidin, indicated the presence of highly polar flavonoid derivatives, such as tri and tetra glycosides. Quercetin and kaempferol, and their glycosides, luteolin, fcrulic acid and protocatechuic acid were identified by TLC cochromatography in various solvents.

The polyphenolic constituents acted as antioxidants as determined by the protection of beta carotene decomposition induced by linolcic acid peroxidation. Thin layer chromatography of LHME and methanol extract of whole lentil was performed using silica gel plates. Samples were dissolved in methanol or water. Plates were developed with chloroform-methanol (12.5% methanol in chloroform, or 25% methanol in chloroform (v/v). After air drying, the plates were exposed sprayed with Folin-Ciocalteau reagent to locate phenolic compounds, or with a solution of linolcic acid and beta carotene to locate antioxidant species, according to the procedure of Mehta et al., J. Agr. Food Chem. (1994) 42:1420–1422. Phenolic species in both LHMEs protected linoleic acid from oxidation. Two prooxidant species that rapidly bleached beta carotene were detected in extract of whole lentil. These were not detected in LHME. Consequently, major prooxidant species of whole lentils are absent from the lentil husk extracts.

d. Fractionation of LHME 7.6 g of green LHME was dissolved in 1 liter of deionized water, then extracted 4 times with 700 ml of ethyl acetate, followed by extraction 4 times with 700 ml butanol. The ethyl acetate extracts and butanol extracts were dried over anhydrous sodium sulflate and concentrated in vacuo. The ethyl acetate extract yielded 220 mg of yellow-brown powder; the butanol extract yielded 887 mg of brown powder. The remaining aqueous extract was concentrated in vacuo and dried to yield 6.121 g of dark brown residue, representing 80% of the starting material. The ethyl acetate, butanol and aqueous fractions of LHME were examined by thin layer chromatography using silica gel plates. The chromatograms were developed with butanol/ethanol/water (4:1:1, v/v) and (4:1:2, v/v) and the spots were visualized using Folin-Ciocalteau and ferric chloride spray reagents. The butanol fraction contained a mixture of dihydroxy and trihydroxy phenols; the ethyl acetate fraction contained mainly dihydroxy compounds, while the aqueous fraction contain highly polar phenolics as glycosides, together with less polar polyhydroxy constituents as found in the other 2 fractions.

To hydrolyze flavonoid glycosides, 2 grams of the aqueous extract residue in 60 ml of 1N HCl were refluxed for 2 hr at 100 C. The hydrolyzate was a deep magenta, indicative of a positive Bate-Smith reaction for proanthocyanidins.

e. Identification of phenolic species

Aglycones were extracted from the hydrolyzate with butanol (4 times with 150 ml). After drying the butanol extract was concentrated in vacuo to yield 715 mg of a magenta powder. Thin layer chromatographic analysis was performed in butanol-acetic acid-water (4:1:2, v/v/v) on silica gel plates. The plates were developed with anisaldehyde reagent to reveal the presence of two procyanidin species and one predominant prodelphinidin species.

EXAMPLE III

FREE RADICAL QUENCHING BY LHME a. Reduction of organic free radical (a,a-diphenyl-B-picrylhydrazyl radical, (DPPH) (Hanto et al. Chem. Pharm. Bull. (1988) 36:2090–2097)).

LHME was dissolved in water and the reduction of DPPH was performed as follows: The 3 ml reaction mixture contained 0.05 mM DPPH in methanol and sample dissolved in water so that the final solvent concentration was methanol-water (1:1, v/v). The concentrations of antioxidant ranged from 0.98 to 500 µg/ml. The decrease in absorbance at 517 nm after 1 minute was recorded.

The IC50 of LHME ranged from 12.58 (±0.17) to 14.83 (±0.21) µg/ml. In contrast, the IC50 of the cotyledon extract was greater than 500. The ethyl acetate extract of LHME exhibited an IC50 of 6.62; the butanol extract, 4.04. For comparison1, the IC50s of the following reference compounds were observed: quercetin: 1.73, (+)catechin: 5.46; gallic acid: 0.63; ascorbic acid: 2.56.

b. Reduction of superoxide

The reduction of superoxide was determined by following the reduction of nitro blue tetrazolium (NBT) by superoxide generated by three systems:

(i) Hypoxanthine-xanthine oxidase and NBT—The reaction mixture contained hypoxanthine: 0.5 mM; xanthine oxidase: 1.67 U/ml: Tris-HCl buffer, pH 7.4: 50 mM, and NBT: 1 mM.

(ii) Xanthine-xanthine oxidase and NBT—The reaction mixture contained xanthine: 0.5 mM; xanthine oxidasc: 1.67 U/ml; Tris-HCl buffer, pH 7.4: 50 mM, and NBT: 1 mM.

(iii) Phenazine methosulfatc (PMS)-NADH and NBT (Yen et al., J. Agric. Food Chem. (1994) 42:629–632) —The reaction mixture contained phenazine methosulfate: 60 µM; NADH: 468 µM; Tris-HCl buffer, pH 7.4, 50 mM; NBT: 1 mM.

LHME was dissolved in Tris HCl at pH 7.4 and added to reaction mixtures over a concentration range from 0.7 to 333.3 µg/ml. Reduction of NBT was followed by recording the absorbance at 560 nm. The following IC50 values were obtained:

For superoxide generated by (i), the IC50 was 4.52 (±0.04) µg/ml, (as compared to 5.5 for ascorbic acid and 1.9 for catechin). For superoxide generated by (ii), the IC50 was 4.16 (±0.12) µg/ml, (as compared to 7.4 for ascorbic acid and 1.8 for catechin). For superoxide generated nonenzymatically by (iii), the IC50 was 4.67 (±0.05) µg/ml—which was the lowest of any reference compound or substance studied, including ascorbic acid (7.0), catechin (40.0), quercetin (21.1), standardized preparation of silymarin (20.4), caffeic acid (47.25), propyl gallate (25.85), ferulic acid (201), gallic acid (19.45), pine bark proanthocyanidins (17.87) and green tea extract (18.8). Because all methods yielded a very low IC50, the results demonstrate an extremely effective quenching of superoxide radicals.

EXAMPLE IV

PRESERVATION OF NUTRIENTS a. Inhibition of the oxidation of essential fatty acids LHME was evaluated according the thin layer chromatography-fluorescent method of Matsuda et al (J. Agric. Food Chem. 1994; 42:1850–6). Briefly, 5 µg of sample dissolved in water was spotted on a silica gel TLC plate, which was sprayed with a 3% solution of linoleic acid in hexane. The plate was dried, then irradiated continuously with UV light at 254 nm. The time required for the fluorescent spots to disappear was considered the induction period for lipid oxidation. The induction period for LHME was 183 minutes, as compared to 70 minutes for alpha tocopherol. Thus, LHME significantly blocked the peroxidation of this essential fatty acid in vitro more effectively than alpha tocopherol.

b. Inhibition of oxidation of vitamin C

Vitamin C (reduced) at a concentration of 40 µg/ml was mixed with equal volumes of antioxidant solutions over a range of 0 to 40 µg/ml in 0.1M potassium phosphate buffer, pH 7.4 (Lau et al., Analyst (1986) 111:665–670). The absorbance at 243 nm was followed at room temperature for 120 minutes. At a concentration of 15 µg/ml, the LHME blocked approximately 90% of the degradation, while proanthocyanidin oligomeric extract from grapeseed extract prevented 75% of degradation and catechin blocked 50% of the degradation. Thus, LHME protects vitamin C in solution from oxidation, providing a greater amount of vitamin C available to work as an antioxidant and polyphenols from the LHME can work synergistically with the vitamin C.

EXAMPLE V

IN VITRO STUDIES a. Inhibiting peroxynitrite-induced apoptosis

Chronic inflammation is related to an overproduction of nitric oxide, which can induce programmed cell death in epithelial cells. Inflammatory mediators, including oxidants, can induce apoptosis. Peroxynitrite is believed to be one of the oxidants formed from excessive superoxide and nitric oxide as produced during chronic inflammation. In vitro systems have been used as models to study the pathophysiology of gut inflammation (Miller et al., Gastroenterology (1995) 109:1475–1483). Programmed cell death, apoptosis, refers to DNA directed nuclear fragmentation associated with cell death, as opposed to cell rupture (necrosis).

The effect of LHME on the inhibition of apoptosis in cultured cell lines induced by oxidative stress was studied in the following experiment. Human T84 epithelial cells, a cancer cell line derived from gut epithelium, were grown in DMEM/F12 medium and maintained in a humidified, 5% carbon dioxide incubator at 37° C. The T84 cells were treated with LHME sterilized by ultrafiltration at final concentrations ranging from 10 to 30 µg/ml and incubated for 4 hr. One group of cells was treated with 100 to 300 µM peroxynitrite, a sufficiently high concentration to induce apoptosis in cells incubated without antioxidants. At the end of the test period, cells were either stained for fragmentation by the TUNEL method, or cytosolic DNA fragments were quantified by a cell death detection ELISA assay. Cell viability was assessed by trypan blue exclusion. LHME consistently protected human cells from peroxynitrite-induced cell death.

b. Toxicity of LHME on established cell lines derived from human colon cancer

The cell lines described above were incubated in the presence of media containing 500 to 2000 µg/ml of LHME. At this level, LHME extract caused necrotic cell death.

c. Selective inhibition of cultured normal macrophages

Normal macrophages (cell line RAW 264.7) were cultured under standard conditions in the presence of 10 µg/ml of LHME. Within 24 hrs., there was significant loss of viability of the macrophages. In contrast, other epithelial cells such as the colonic epithelial T84 cells were unaltered by the presence of LHME at a concentration of 30 µg/ml when incubated up to 5 days.

While certain preferred embodiments of the invention have been heretofore described, the invention is not to be construed as so limited, except to the extent such limitations are found in the claims.

What is claimed is:

1. An extract of lentil seed coat, wherein said extract has a phenolics content in the range of from about 1 to about 6 milligrams of catechin equivalents per 10 milligrams of extract.

2. An extract of lentil seed coat as in claim 1 wherein said extract has a phenolics content in the range of from about 2 to about 4 milligrams of catechin equivalents per 10 milligrams of extract and said seed coat is from Lens esculenta.

3. An extract of lentil seed coat as in claim 2 wherein the phenolics comprise polyphenols.

4. An extract of lentil seed coat as in claim 3 wherein the polyphenols include flavonoids and phenolic acids.

5. An extract of lentil seed coat as in claim 4 wherein the flavonoids are selected from the group consisting of flavones, flavanols and condensed tannins.

6. An extract of lentil seed coat as in claim 5 wherein the flavones comprise luteolin.

7. An extract of lentil seed coat as in claim 6 wherein the flavanols are selected from the group consisting of quercetin and kaempferol.

8. An extract of lentil seed coat as in claim 5 wherein the condensed tannins comprise proanthocyanidins.

9. An extract of lentil seed coat as in claim 8 wherein the proanthocyanidins are selected from the group consisting of procyanidin, prodelphinidin, a glycoside of procyanidin, and a glycoside of prodelphinidin.

10. An extract of lentil seed coat as in claim 4 wherein the phenolic acids are selected from the group consisting of ferulic acid, protocatechuic acid, and caffeic acid.

11. An extract of lentil seed coat as in claim 1 wherein a plurality of prooxidant species found in extract of whole lentil is substantially absent in said extract of lentil seed coat.

12. An extract of lentil seed coat as in claim 1 wherein said extract has an IC50 in the range of from about 1.5 to about 15 micrograms per milliliter as measured by reduction of dipicrylhydrazyl radical.

13. An extract of lentil seed coat as in claim 12 wherein said extract has an IC50 in the range of from about 4.04 to about 14.83 micrograms per milliliter as measured by reduction of dipicrylhydrazyl radical.

14. An extract of lentil seed coat as in claim 1 wherein said extract has an IC50 in the range of from about 1 to about 10 micrograms per milliliter as measured by reduction of nitro blue tetrazolium by superoxide.

15. An extract of lentil seed coat as in claim 14 wherein said extract has an IC50 in the range of from about 3 to about 6 micrograms per milliliter as measured by reduction of nitro blue tetrazolium by superoxide.

16. An extract of lentil seed coat as in claim 15 wherein said extract has an IC50 in the range of from about 4 to about 5 micrograms per milliliter as measured by reduction of nitro blue tetrazolium by superoxide generated non-enzymatically in a phenazine methosulfate-NADH-NBT system.

17. An extract of lentil seed coat as in claim 9 wherein at least 50% by weight of the proanthocyanidin comprises prodelphinidin.

18. An extract of lentil seed coat as in claim 17 wherein at least 70% by weight of the proanthocyanidin comprises prodelphinidin.

19. An extract of lentil seed coat as in claim 18 comprising at least 15% by weight of prodelphinidin.

20. An extract of lentil seed coat as in claim 19 comprising at least 20% by weight of prodelphinidin.

21. An extract of lentil seed coat as in claim 2 consisting essentially of kaempferol, quercetin, proanthocyanidins, and phenolic acids.

* * * * *